United States Patent
Tung

(10) Patent No.: US 6,652,095 B2
(45) Date of Patent: Nov. 25, 2003

(54) ORTHOKERATOLOGY AND BI-FOCAL CONTACT LENS

(76) Inventor: Hsiao-Ching Tung, 2F, No. 164, Ling Jiang Street, Taipei (TW)

( * ) Notice: Subject to any disclaimer, the term of this patent is extended or adjusted under 35 U.S.C. 154(b) by 0 days.

(21) Appl. No.: 10/214,652

(22) Filed: Aug. 7, 2002

(65) Prior Publication Data

US 2002/0186344 A1 Dec. 12, 2002

Related U.S. Application Data

(63) Continuation-in-part of application No. 09/715,964, filed on Nov. 17, 2000, now Pat. No. 6,543,897.

(51) Int. Cl.⁷ .................................................. G02C 7/04
(52) U.S. Cl. ...................... 351/161; 351/160 R; 351/177
(58) Field of Search ........................ 351/160 R, 160 H, 351/161, 162, 177

(56) References Cited

U.S. PATENT DOCUMENTS

| | | | |
|---|---|---|---|
| 4,952,045 A | 8/1990 | Stoyan | 351/160 R |
| 5,191,365 A | 3/1993 | Stoyan | 351/160 R |
| 5,349,395 A | 9/1994 | Stoyan | 351/160 R |
| 5,963,297 A | 10/1999 | Reim | 351/160 R |

*Primary Examiner*—Scott J. Sugarman
(74) *Attorney, Agent, or Firm*—Philip K. Yu; Birch Stewart LLP

(57) ABSTRACT

A contact lens is fitted to a cornea of a patient's eye to gradually alter the patient's cornea during continued wear to reshape the cornea to reduce the hyperopia and/or presbyopia condition. The contact lens has a plurality of zones that includes one or two optical zones, a plateau zone, a fitting zone, an alignment zone and a peripheral zone. The one or more optical zones are utilized to redistribute cornea tissue to cause the cornea to have a steepened central portion surrounded by a flat mid-peripheral ring The plateau zone helps steepening the central cornea by two ways: a positive molding effect of pushing the cornea tissue inward to pile up and a negative molding effect to flatten the mid-peripheral cornea for enhancing.

20 Claims, 4 Drawing Sheets

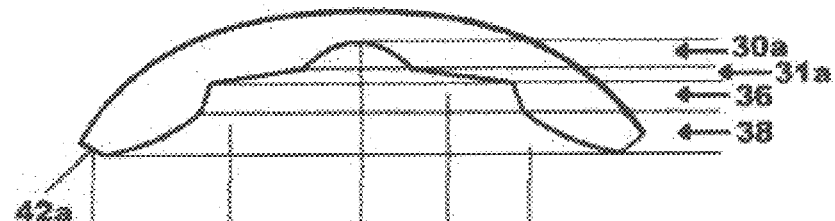
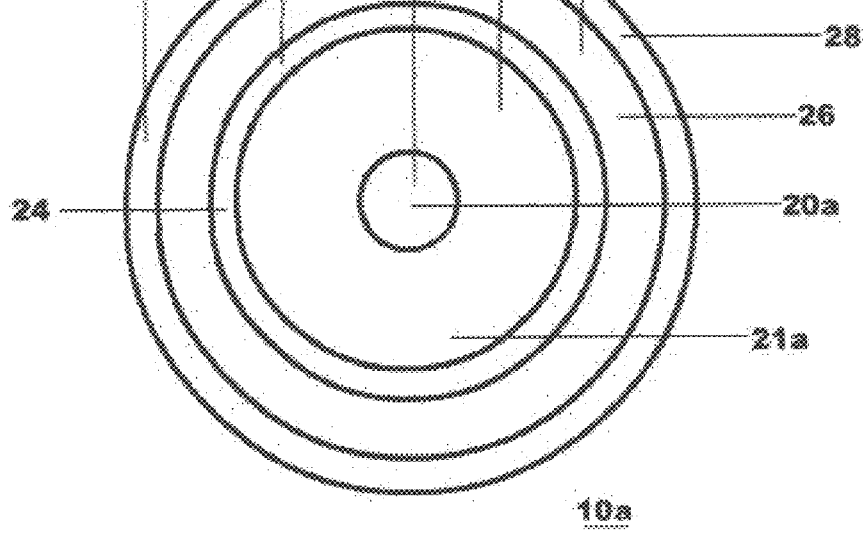
Fig. 5
Fig. 4

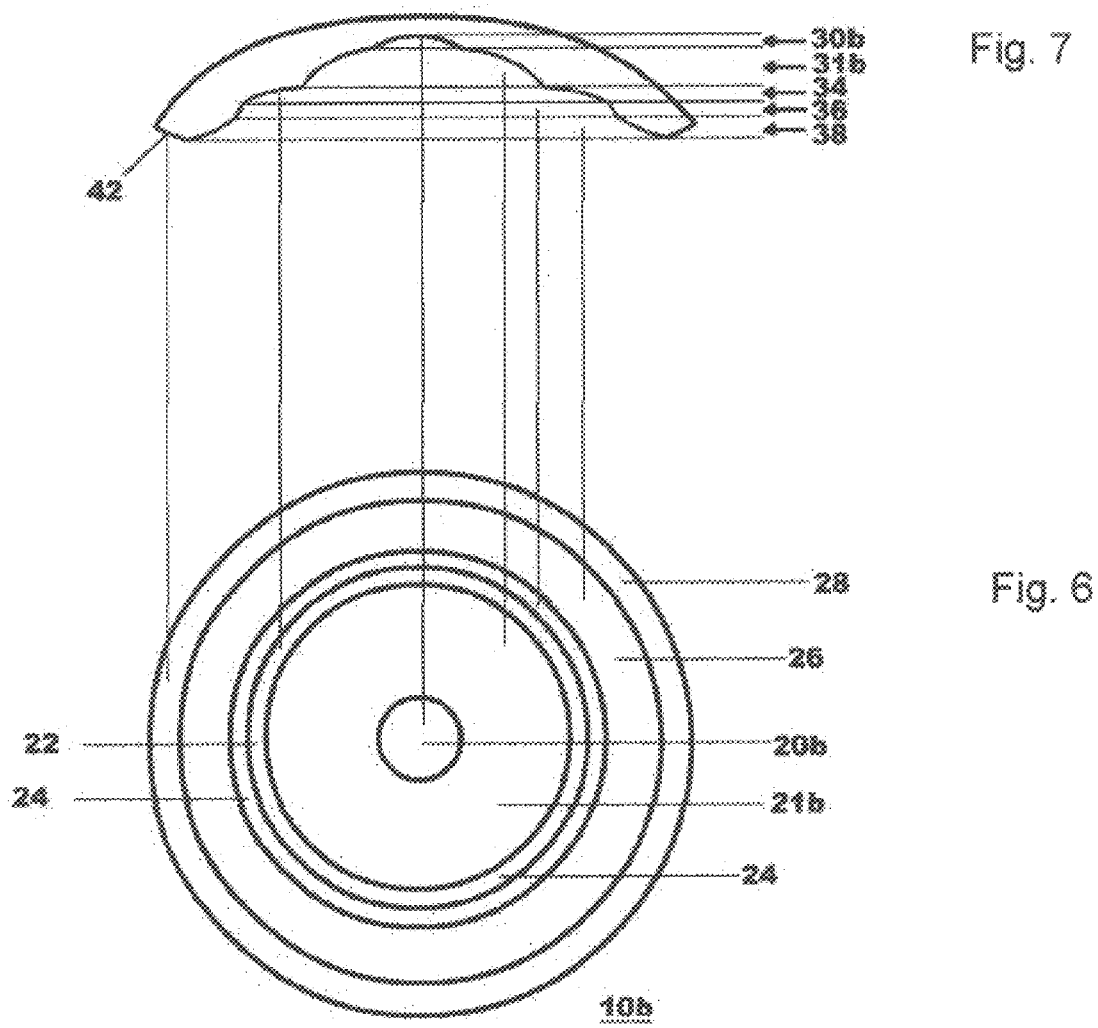

ent by ortho-k is dependent upon the shape and structure of the contact lens. For example, conventional contact lenses with a longer central radius of curvature than the central radius of the cornea are known to change the shape of the cornea by compressing the surface at its apex. This reshaped cornea has a lengthened radius of curvature in its central zone, which serves to improve myopia. Although it has been well known to treat myopia using modem Ortho-K lenses to reshape the cornea, treating hyperopia or presbyopia using Ortho-K lenses has been met with uncertain outcome and results.

ORTHOKERATOLOGY AND BI-FOCAL CONTACT LENS

RELATED APPLICATION

The present invention is a continuation-in-part of a application, Ser. No. 09/715,964, filed Nov. 17, 2000, by the inventor hereof, entitled ORTHOKERATOLOGY CONTACT LENS, now U.S. Pat. No. 6,543,897, whose disclosure is incorporated by this reference as though set forth fully herein.

BACKGROUND OF THE INVENTION

1. Field of the Invention

The present invention relates to contact lenses that are used in treating hyperopia and presbyopia, and more particularly, to contact lenses that are shaped to provide gradual altering of the patient's cornea during continued wear to reshape the cornea to reduce the hyperopic and presbyopic condition.

2. Description of the Related Art

Many people experience difficulties with their vision due to a number of possible conditions. The most common vision problem is a condition known as myopia or near-sightedness. Myopia is a common condition where an eye cannot focus on far-away objects because the cornea of the eye is curved too steeply (i.e., where the radius of curvature of the cornea is smaller than normal) to provide adequate focusing at the retina of the eye. Another condition is known as hyperopia or farsightedness. With hyperopia, the eye cannot focus on both far and near objects because the curvature of the cornea of the eye is too flat (i.e., where the radius of curvature of the cornea is larger than normal)to provide adequate focusing at the retina of the eye. Hyperopia is common among young children. Severe hyperopia will induce lazy eye or amblyopia in childhood. Mild or moderate hyperopia is tolerable and insidious in young ages but will cause reading problems in older age. Another common problem is astigmatism, where unequal curvature of one or more refractive surfaces of the cornea prevents light rays from focusing clearly at one point on the retina, resulting in blurred vision. Presbyopia is the most common vision problem in adults 40 years and older. It does not matter whether they are emmetropic, myopic or hyperopic in far vision, the middleaged population over 40 years old will begin to experience difficulty in focusing on close objects, due to the loss of flexibility of the eye's crystalline lens. Presbyopia may occur and complicate other refractive problems such as hyperopia, myopia or astigmatism.

Hyperopia and presbyopia are both conditions for which no entirely suitable permanent treatment has been developed. The conventional way is to wear a pair of heavy convex glasses. One approach to correcting hyperopia is through laser surgical reshaping of the cornea. However, such surgical procedures have not been entirely safe and there have been less favorable vision outcome for the hyperopia surgery than that of myopia surgery.

Another approach to treating some or all of these conditions is to alter the corneal shape by wearing contact lenses which are designed to continually exert pressure on selected locations of the cornea to gradually force or mold the cornea into the desired normal corneal curvature. A retainer lens is then worn on a part-time basis to prevent the cornea from returning to its previously deformed shape. This method of treatment is commonly referred to as orthokeratology (referred to herein as "ortho-k"). The success of any treatment by ortho-k is dependent upon the shape and structure of the contact lens. For example, conventional contact lenses with a longer central radius of curvature than the central radius of the cornea are known to change the shape of the cornea by compressing the surface at its apex. This reshaped cornea has a lengthened radius of curvature in its central zone, which serves to improve myopia. Although it has been well known to treat myopia using modem Ortho-K lenses to reshape the cornea, treating hyperopia or presbyopia using Ortho-K lenses has been met with uncertain outcome and results.

Ortho-k has been performed in some form or another since the early 1970s. There are three factors that impact the effectiveness and desirability of ortho-k procedures and lenses. The first factor is the time needed to achieve a desired visual correction. Unfortunately, the time needed to achieve a desired visual correction using conventional ortho-k techniques and lenses has been a serious problem, since it will take several months, or even years, for small amount of hyperopia to be reduced. The second factor is the amount of hyperopia that can be corrected using ortho-k. Conventional ortho-k techniques and lenses were limited to a reduction of no more than about one diopter of hyperopia. The third factor is the amount of time that the correction would "hold" before degrading (known as the "maintenance period"). Conventional ortho-k techniques and lenses provide variable length for the maintenance period. To prolong this maintenance period, a patient would have to wear a retainer lens.

Some patients have been fitted with a series of progressively steeper regular RGP lenses to treat hyperopia. The lens diameter was small (7–8 mm) and the base curve steeper than the central cornea curvature. Lenses would need to be replaced upon the showing of some effect, while the results are usually minimal and unpredictable. The lenses sometimes became tightened to cause adverse effect.

U.S. Pat. No. 5,963,297 to Reim and U.S. Pat. Nos. 5,349,395, 4,952,045, 5,191,365, 6,010,219 to Stoyan disclose Ortho-k lens designs for myopia reduction. There has been no lens specifically designed for increasing the curvature power of the cornea for hyperopia reduction. Orthokeratology for the presbyopia has never been addressed or mentioned before, largely because it was thought that no lens could mold a cornea into dual shapes for clearing up near, as well as far, vision simultaneously. The conventional way to treat a myopic, and yet presbyopic, person by Ortho-k is either to sacrifice the far vision of both eyes (under-corrected) or to sacrifice monocular far vision (Mono-vision). Both ways make it hard to be accepted by most of the patients.

Notwithstanding the improvements provided by modem Orthokeratology for myopia, there remains a need for a contact lens that can be used for effective ortho-k of hyperopia and/or presbyopia.

SUMMARY OF THE INVENTION

It is an object of the present invention to provide an ortho-k contact lens that provides effective reduction of hyperopia and/or presbyopia.

It is another object of the present invention to provide an ortho-k contact lens that provides a shorter correction time.

It is yet another object of the present invention to provide an ortho-k contact lens that provides a longer maintenance period.

The objects of the present invention may be achieved by providing an apparatus and method for correcting a hyperopia and/or presbyopia condition in a patient's eye. In accordance with a method of the present invention, a contact lens is fitted to a cornea of a patient's eye, the contact lens having a plurality of zones that includes a optical zone, a Plateau zone, a fitting zone, an Alignment zone and the peripheral zone. The Plateau zone is carefully created to flatten the mid-peripheral cornea curvature to cause the cornea to have a flattened mid-peripheral portion surrounding the central steeper cornea zone. The flatter mid-peripheral plateau zone works together with the steeper optical zone to enhance the steepening of the central cornea to reduce hyperopia. The concept of "flattening the mid-peripheral cornea to enhance the steepening of the central cornea for effective hyperopia reduction" is totally different from that of the conventional method by "squeezing the cornea tissue inward and piling up to steepen the central cornea for hyperopia reduction". We define the new concepts to be a "dual molding" for hyperopia and/or presbyopia reduction.

In accordance with an apparatus of the present invention, a contact lens is provided having a base curve portion of the lens, a plateau curve portion of the lens circumscribing and coupled to the base curve portion, a fitting curve portion of the lens circumscribing and coupled to the plateau curve portion, and an alignment curve portion of the lens circumscribing and coupled to the fitting curve portion, and a peripheral curve portion of the lens circumscribing and coupled to the alignment curve portion.

The goal of this type of lenses is to mold the cornea into a shape of central steepening just like a hummock on top of a plateau. The overall diameter of the central optical zone could be varied or divided for different purposes of correcting hyperopia or presbyopia.

For treating the hyperopic person, the base curve should preferably be steeper than the central cornea curvature. The optical zone should be wide enough for better far vision. It is also preferred to keep the plateau zone as narrow as possible to prevent it from inducing ghost imaging due to the flattened mid-peripheral area.

For treating the presbyopic person, the optical zone should be divided into two portions. The central zone should be designed to be very small for the purpose of near vision to prevent it from hindering the far vision. The outer optical zone then should be much wider to mold the juxta-central cornea area into a flatter zone to clear up far vision (reducing myopia, hyperopia, or astigmatism if any).

BRIEF DESCRIPTION OF THE DRAWINGS

FIG. 4 is a front planar view of the ortho-k contact lens according to another embodiment of the present invention for presbyopia correction in a myopic person.

FIG. 5 is a side sectional view of the ortho-k contact lens of FIG. 4.

FIG. 6 is a front planar view of the ortho-k contact lens according to one embodiment of the present invention for presbyopia correction in a hyperopic person.

FIG. 7 is a side sectional view of the ortho-k contact lens of FIG. 6.

DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
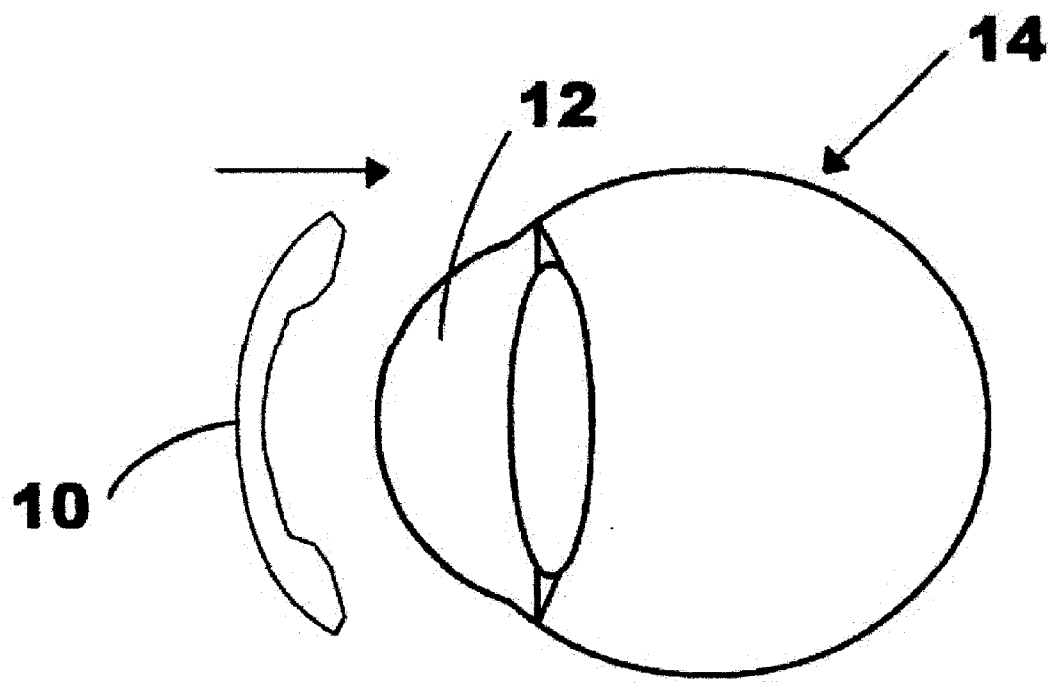
FIG. 1 is a side schematic outline view of an ortho-k contact lens according to the present invention in use with a cornea of a patient's eye.
Figure 3:
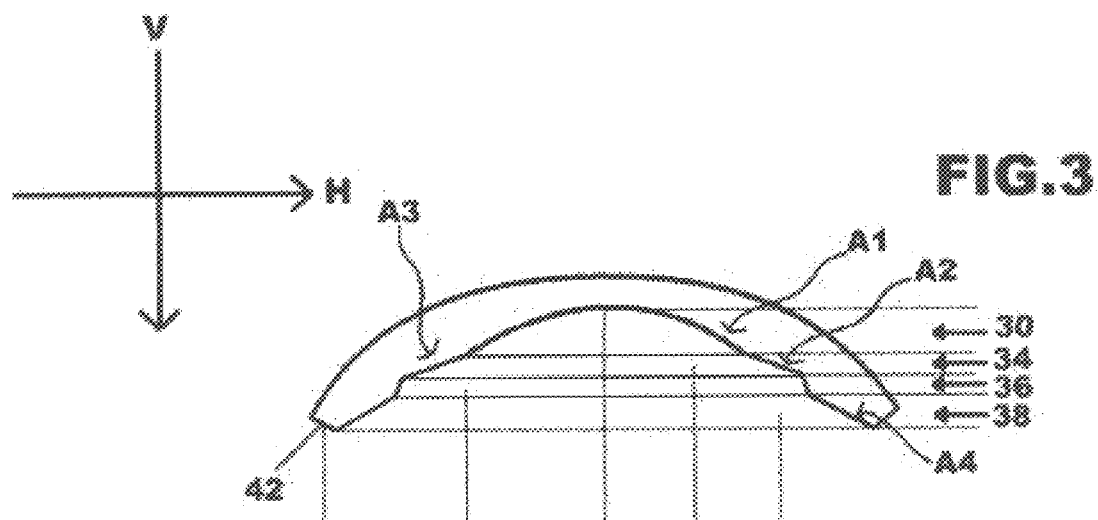
FIG. 3 is a side sectional view of the ortho-k contact lens of FIG. 2.
Figure 2:
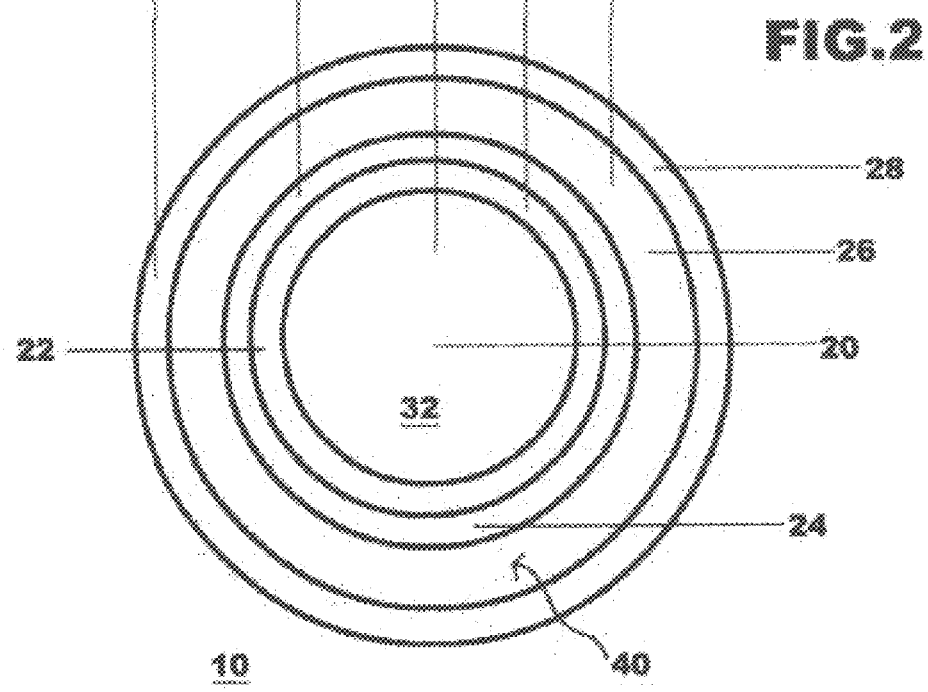
FIG. 2 is a front planar view of the ortho-k contact lens according to one embodiment of the present invention for hyperopia correction.

FIGS. 1–3 illustrate an ortho-k contact lens 10 according to one embodiment of the present invention. As shown in FIG. 1, the contact lens 10 is a dual geometric contact lens that is adapted to be worn over the cornea 12 of a patient's eye 14. The contact lens 10 has five correction zones, listed from the center of the lens 10 to the outer periphery: an optical zone 20, a plateau zone 22, a fitting zone 24, an alignment zone 26, and a peripheral zone 28.

Optical Zone

Referring to FIGS. 2 and 3, the optical zone 20 has a curvature that is defined by the base curve 30. The optical zone 20 forms a suitable space for molding tissue to a region substantially centered at the apical center of the cornea 12, and is responsible for the corrective steepening or increasing in the radius of curvature of the central cornea during treatment. The radius of curvature of the base curve 30 is smaller than a measured curvature of a central portion of the cornea 12 for treatment of hyperopia, thus creating a central tenting up area 32. The tent-up area 32 provides a suitable space for piling the cornea tissue up during vision correction.

The optical zone in the invention may be divided into two portions for the treatment of presbyopia coupled with hyperopia. A tiny inner additive optical curve 30b defined by inner additive optical zone 20b is steeper (shorter radii) than the consecutive outer base curve 31b by 1–4 Diopters. The outer base curve 31b defined by the outer optical zone 21b is steeper (shorter radii) than the central curvature of the cornea 12 by 1–15 diopters. The tented-up spacing under the outer optical zone 21b causes the cornea molding to form a steeper juxta-central portion of the cornea 12 for correcting hyperopia, and the even steeper inner optical zone 20b causes the formation of even steeper curvature of the central portion of the cornea 12 for correcting presbyopia. The inner optical zone 20b is preferably kept small enough to prevent it from hindering the far vision and the size is usually from 0.5 to 1.5 mm. As can be appreciated by those skilled in the art, the pupil of human eyes will constrict for near reading (so called "near reflex") and dilate when looking into the distance. Since the tiny central blurred image will be neglected when looking into far distance, we can create a tiny (0.1–1.5 mm) steeper inner optical zone 20a, 20b coupled with a wider (1.5–4.0 mm) and flatter outer optical zone 21a, 21b to treat the far and near vision simultaneously in one lens.

The steeper inner optical zone 20a of FIG. 6 can also be incorporated into a single reverse geometric Ortho-K lens to treat coexisting presbyopia and myopia simultaneously. In this situation, the inner base curve 30a, defining the inner optical zone 20a, is made 1–4 diopters (hereinafter "D") steeper than the outer base curve 31a, defining the outer optical zone 21a, to mold the central portion of the cornea 12 into a steeper curvature for reading. The outer optical zone 21a and outer base curve 31a is determined according to the principle of optical zone/curvature of the reverse geometric ortho-K lenses for proper myopia reduction. The incorporated inner optical zone 20a has an inner base curvature 30a that is 1–4 D steeper (shorter radius) than the consecutive outer base curve 31a of outer optical zone 21a. The inner additive base curve 30a is not necessarily steeper (shorter radius), but is preferably flatter (longer radius) than the curvature of the central portion of the cornea 12, except when the myopic power is mild and numerically smaller than that of the presbyopic additive power which in turn could be same as, or slightly steeper (shorter radii) than, the curvature of the central portion of the cornea 12. The outer base curve 31a, functioning like the central optical zone/base curve of a reverse geometric Ortho-K lens for myopia reduction, is flatter (larger radius) than the central portion of the cornea 12 by 1–30 D, and is designed to compress the juxta-central portion of the cornea 12 for proper myopia reduction.

There could be a substitution for dividing the optical zones for presbyopia reduction, by creating an aspheric base curve with positive eccentricity (e-value), so that the curvature of the inner portion of base curve 30 will be substantially steeper than that of the outer portion of the base curve 30. The curvatures flatten (elongate) continuously from the lens center to the edge of optical zone 20 due to the eccentricity (e-value). That will then mold the cornea into a shape of a steeper central portion for the near vision and a flatter juxta-central portion for the far vision.

In one embodiment of the present invention, the diameter of the optical zone 20 ranges from 3 mm to 8 mm, and the inner optical zone 20a, 20b ranges from 0.5 mm to 1.5 mm, the outer optical zone 21a, 21b ranges from 1.0 mm to 4.0 mm, and the radii of the curvature for the base curve 30 and the inner base curve 30a, 30b and the outer base curve 31a, 31b ranges from 15.0 mm to 5.0 mm.

Plateau Zone 22

Referring to FIGS. 2, 3, 4 and 5, the Plateau zone 22 has a radius of curvature defined by a predefined plateau curve 34, which is longer (i.e., flatter) than the radius of curvature associated with the base curve 30 or outer base curve 30a. On the lens 10a for the reduction of myopia coupled with presbyopia, the flatter plateau zone in lens 10a merges with the flatter outer optical zone 31a and can be looked upon as a continuous and gradual-flattening curve with positive e-value.

This longer radius of curvature of the plateau zone 22 defines a plateau curvature 34 that is flatter (longer radius) than the measured curvature of the central portion of the cornea 12 and the measured curvature of the portion of the cornea 12 circumscribing the central portion of the cornea 12. As mentioned above, the plateau zone 22 functions as a primary compression force to the mid-peripheral cornea region substantially surrounding the apical central cornea between the inner and outer optical zones 20, 21a, 21b and the fitting zone 24.

The plateau zone 22 is preferably kept as narrow as possible, so that it can function as a compression zone for mid-peripheral cornea flattening. The flattened mid-peripheral cornea will in turn enhance the central cornea 12 for further steepening. The molding technique is named "dual molding" which includes a positive molding for central cornea steepening and a negative molding for mid-peripheral cornea flattening. The lens design can also be named a "dual geometric lens" which include a positive geometric zone and a negative geometric zone for the steeper optical zone and flatter plateau zone respectively. A narrow flattened mid-peripheral cornea area coupled with a large steepened central and juxta-central cornea area will prevent the person from being bothered by ghost image in far vision.

As can now be appreciated, the plateau zone 22 performs three primary functions. First, the provision of the plateau zone 22 allows an effective compression on mid-peripheral cornea to push the cornea tissue inward, which in turn steepens the cornea curvature of the central portion of the cornea 12. This represents the positive molding component of the "dual molding". The compression force exerted by the flatter plateau zone 22 on mid-peripheral cornea portion will be far more effective for tissue molding than the compression force by traditional method of a series of steeper regular RGP. The compression force by a steep fit regular RGP is exerted on more peripheral cornea and is more tangential to the compressed area, so that most of the molded tissue will pile up at mid-peripheral area instead of the central area to cause an adverse effect.

Second, the plateau zone 22 functions as a compression zone for the effective flattening of the mid-peripheral area surrounding the steepened central cornea area 12. Forming a plateau shape on the mid-peripheral area of the cornea 12 by the compression force of plateau zone 22 will in turn enhance the steepening effect of the central cornea. The negative molding component of "dual molding" flattens the mid-peripheral cornea 12 and effectively enhances the positive molding of steepening the central and juxta-central portion of the cornea 12. The flatter plateau zone will also prevent the cornea tissue, which is squeezed inward by the alignment zone 26 (described later), from piling up at the mid-peripheral area. Piling up of the cornea tissue on the mid-peripheral area would have adversely flattened the central cornea curvature and increased the hyperopia, instead of reducing it. This is one of the problems that conventional orthokeratology frequently encountered.

Third, the flat plateau curve 34 of the plateau zone 22 reserves more room for the vertical height of the fitting zone 24 so that the fitting curve 36 can be fitted much steeper than the plateau curve 34. This allows the fitting curve 36 to form a space for proper tear circulation and a room for tissue molding before connecting to the alignment zone 26 (described later).

In one embodiment of the present invention, the diameter of the plateau zone 22 ranges from 0. 1 mm to 2.0 mm. The radius of curvature for the plateau curve 34 is flatter (longer radius) than the central base curve 30 or outer base curve 31b by 3–30 diopters, and is usually between 8–25 diopters. In lens 10a, the plateau zone 22 and plateau curve 34 merges with the outer optical zone 21a and outer base curve 31a, respectively.

Although the present invention illustrates the provision of one plateau curve 34, it is also possible to provide the contact lens 10 with two or more plateau zones and curves as well as substitute the zone with an aspheric curve of a positive e value, or even merge with zone 21a or zone 21b to form a continuously flatter curvature next to the inner optical zone 20a or 20b.

Fitting Zone 24

Referring to FIGS. 2 and 3, the fitting zone 24 of lens 10 has a radius of curvature defined by a fitting curve 36 with the radius of curvature being less than (i.e., shorter than) the radius of curvature associated with the plateau curves 34. Since the plateau zone and curve in lens 10a (shown in FIGS. 4 and 5) merge with the outer optical zone 21a and outer base curve 31a, the plateau curve 34 in lens 10a can then be looked upon as having the same definition of outer optical zone 21a and outer base curve 31a for lens 10a shown in FIGS. 4 and 5. This shorter radius of curvature of the fitting zone 24 yields a fitting curvature 36 that is much steeper than the plateau curve 34. Although the fitting curve 36 is much steeper (smaller radius) than the plateau curves 34, the curvature 36 may not necessarily be steeper than the measured curvature of the central portion of the cornea 12, or the measured curvature of the portion of the cornea 12 circumscribing the central portion of the cornea 12.

The fitting zone 24 acts as a transition region between the plateau zone(s) 22 and the alignment zone 26. The fitting zone 24 brings the posterior surface of the contact lens 10 to a bearing relationship on the mid-peripheral portion of the cornea 12 under the plateau zone 22, and provides compression force on the plateau zone 22, thereby compressing the mid-peripheral portion of the cornea 12, for dual molding of the cornea 12. In one embodiment of the present invention, the width of the fitting zone 24 ranges from 0.1 mm to 2.0 mm, the radius of curvature for the fitting curve 36 is 5–30 diopters steeper than the plateau curve 34, and is 15 diopters flatter to 15 diopters steeper than the base curve.

At this time, it should be noted that a lens can be calculated from the view point of saggital depth. A saggital depth calculation translates the component curvatures and each width for a lens into a simple factor known as the saggital depth. A saggital depth will be measured from the center of a lens to the denoted width, and will also define the slope of an area on a lens. In other words, the angles A1, A2, A3 and A4 illustrated in FIG. 3 can be calculated as the "saggital depth/zone width" and can be considered to be a slope ratio, which can be defined as the vertical height/zone width. Since a dual geometric lens has multiple curvatures, we have to calculate the vertical height of each zone and add them up. Here, the summation of (i) vertical height of the optical zone 20, (ii) the vertical height of the plateau zone 22, and (iii) the vertical height of the fitting zone 24 should be equal to the height of the original cornea with the same zone width (i.e., the 3 total zones) plus 10 microns (this additional 10 microns is an allowance made to prevent the lens 10 from bearing on the cornea 12). This is the underlying principle of saggital depth calculation. A more detailed explanation of saggital depth calculation is provided in ADVANCED CL FITTING, PART SEVEN, TRENDS IN MODERN ORTHOKERATOLOGY, Optician, No. 5645, Vol. 215, Apr. 3, 1996, pages 20–24, whose entire disclosure is incorporated by this reference as though fully set forth herein.

Alignment Zone 26

Referring to FIGS. 2 and 3, the alignment zone 26 is designed to provide and maintain centration of the lens 10 by having a radius of curvature that is either the same as, or slightly longer than the central curvature of the cornea 12 (i.e., to match the peripheral cornea). A predefined alignment curve 38 defines the curvature of the alignment zone 26, which is almost the same as the measured curvature of the portion of the cornea 12 circumscribing the central portion of the cornea 12.

The alignment zone 26 creates a large bearing area 40 in a region corresponding with the portion of the cornea 12 where a centering force is created that maintains the optical zone 20 substantially at the apical center of the cornea 12. The alignment zone 26 further produces a secondary compressive force in the large bearing area 40 that cooperates with the primary compressive force from the plateau curve to flatten the mid-peripheral portion of the cornea 12 contributes to the negative molding component of the dual molding for hyperopia and/or presbyopia reduction during vision correction.

The alignment curve 38 is determined by mean K (also known as KM). In other words:

a. (Vertical KM+Horizontal KM)/2.

The central mean K in turn will be recalculated to estimate the mid-peripheral radius of curvature according to the eccentricity (e-value) of a cornea to match the point that the alignment zone 26 contacts the cornea 12. This calculation method enjoys two benefits over known methods. First, this calculation method can be used for both toric (astigmatic) or non-toric corneas. Corneas with the same horizontal central KM do not mean they should be fitted with the same ortho-k lens. The vertical curvature could be different (astigmatic or toric cornea), the e-value could also be different, and they should be considered as different corneas. Second, by considering the e-value of a normal cornea, the peripheral attachment of the alignment zone 26 will be improved.

The associated alignment curve 38 creates a bearing zone over a large surface area of the cornea 12, which is helpful in aligning the lens 10 at the apex of the cornea 12. In one embodiment of the present invention, the width of the alignment zone 26 ranges from 0.1 mm to 5.0 mm (depending on the fitting characteristics desired and the particular shape factors of the cornea 12), the radius of curvature for the alignment curve 38 is 1–30 diopters steeper than the plateau curve 34, and the alignment curve 38 is also about 1–25 diopters less steep (i.e., flatter) than the fitting curve 36.

Alternatively, the alignment zone 26 can be segmented into multiple curves and any combination of any shapes or curves, as long as sufficient bearing area is maintained.

Peripheral Zone 28

The peripheral zone 28 is designed with a radius of curvature longer than that of the cornea 12, yielding a curvature less than a measured curvature of a portion of the cornea 12 circumscribing the central portion of the cornea 12 that corresponds to the alignment zone 26. The peripheral zone 28 has its surface contour defined by a predefined peripheral curve 42 which has a curvature that nearly parallels the portion of the cornea 12 underneath it, but is flatter than the cornea 12. The peripheral zone 28 promotes tear flow under the contact lens 10 by taking advantage of a tear pumping action created when the individual blinks the eyelid. This tear flow allows constant lubrication and oxygenation of the lens-cornea interface and results in a more comfortable and wearable lens 10.

Additionally, the peripheral zone 28 is designed to create a slight edge lift which allows easy contact lens removal from the cornea 12. In one embodiment of the present invention, the width of the peripheral zone 28 ranges from 0.1 mm to 2.0 mm, the radius of curvature for the peripheral curve 42 is 0–15 diopters greater (flatter) than the plateau curve 34, and is also about 1–35 diopters greater (longer radii) than the fitting curve 36, or the alignment curve 38. The peripheral curvature should be carefully calculated according to the aforementioned saggital theory to achieve an edge lift of 100–120 microns. An overly-large edge lift may induce a reverse suction force to create air bubbles under the lens 10, while an overly-small edge lift may reduce tear circulation and cause lens seal-off.

The different radii used to define the base curve 30, the plateau curve 34, the fitting curve 36, the alignment curve 38 and the peripheral curve 42 are calculated after careful examination of the patient's eye and the associated ocular tissue. The corneal curvature must be measured, the proper contact lens power defined, and the anticipated physiological response to the contact lens 10 must be determined. An individual skilled in the examination techniques of the ocular system is typically capable of performing these tasks.

As explained above, the provision of one or more plateau zones 22 offers dual molding force to facilitate the steepening of the central portion of the cornea 12 for hyperopia and/or presbyopia correction. The invention of a tiny and steeper inner optical zone 30a, 30b open up a new era of correcting dual refraction errors of presbyopia coupled with hyperopia, or presbyopia coupled with myopia simultaneously in one lens. The present invention enables treatment of dual refractive problems in one lens by dual molding force from a dual geometric lens. A typical dual geometric lens will have consecutive curvatures featuring interlaced steep-flat-steep-flat curvatures from the central portion outward. Of course, there can be additional zones or eccentricity (e-value) incorporated into the basic components as previously mentioned.

For example, the contact lens 10 of the present invention can achieve a reduction of hyperopia up to 2.0–10.0 diopters with a shorter wearing time (e.g., 6–10 hours a day for initial wearing, and 4–8 hours a day to maintain) and longer maintenance period (e.g., 1–7 days after the lens 10 is removed).

EXAMPLE 1

A contact lens having the following dimensions was provided for a AA0786 patient:

<Right Eye>

KM: 43.375 D(7.78 mm)@H, 44.5 D(7.85 mm)@V

Refraction: +2.00–0.75@130(hyperopia+2.00D astigmatism 0.75D axis 130)

optical zone 20: width 4.0 mm, radius of curvature 7.25 mm plateau zone 22: width 1.1 mm, radius of curvature 9.79 mm fitting zone 24: width 0.5 mm, radius of curvature 6.57 mm alignment zone 26: width 1.2 mm, radius of curvature 7.85 mm peripheral zone 28: width 0.4 mm, radius of curvature 11.30 mm <Left Eye>

KM: 43.375 D(7.78 mm)@H,44.5 D(7.85 mm)@V

Refraction: +3.00–1.00@40 (hyperopia+3.00D and astigmatism 1.00D axis 40 degree)

optical zone 20: width 4.0 mm, radius of curvature 7.16 mm plateau zone 22: width 1.1 mm, radius of curvature 9.85 mm fitting zone 24: width 0.5 mm, radius of curvature 6.59 mm alignment zone 26: width 1.2 mm, radius of curvature 7.85 mm peripheral zone 28: width 0.4 mm, radius of curvature 11.30 mm The contact lenses were worn by the patient for 7 day, at 7–8 hours a day.

After this correction period, the patient experienced a hyperopia and astigmatism reduction to zero power. This is equivalent to a hyperopia reduction of +1.75 D for the right eye and +2.50D (spherical equivalent) for the left eye. The maintenance period (of nearly zero power) lasted for all awakening hours with a 5–7 hour maintenance night wearing. The topography of the cornea is well-centered and has a definite boundary of a hummock-on-plateau shape to support an efficient reduction in hyperopia. This case has been followed for 3 months with no side effects.

EXAMPLE 2

A contact lens having the following dimensions was provided for a AA0751 patient:

<Right Eye>

KM: 42.25(7.99 mm), 43.125(7.83 mm)

Refraction: −3.00–0.50@90(myopia−3.00D astigmatism 0.50D axis 90 degree)

With Presbyopic Near addition of +1.50D, corrected to 20/20 at 40 cm (Since the right eye is the sighting eye for far, we designed a reverse geometric lens for right eye to correct her myopia only)

optical zone: width 5.6 mm, radius of curvature 8.89 mm fitting zone : width 0.8 mm, radius of curvature 7.04 mm alignment zone: width 1.5 mm, radius of curvature 8.03 mm peripheral zone: width 0.4 mm, radius of curvature 11.80 mm <Left Eye>

KM: 42.00 D(8.04 mm)), 42.65 D(7.91 mm)

Refraction: −3.00–0.50@75(myopia−3.00D and astigmatism 0.50D axis 40 degree)

With presbyopic near addition of +1.50D, corrected to 20/20 at 40 cm (We corrected her left eye for myopia as well as presbyopia simultaneously)

inner optical zone 20a: width 1.0 mm, radius of curvature 8.50 mm outer optical zone 21a: width 2.50 mm, radius of curvature 8.83 mm plateau zone 22: none (merged with outer optical zone 21a)

fitting zone 24: width 0.6 mm, radius of curvature 6.85 mm alignment zone 26: width 1.5 mm, radius of curvature 8.07 mm peripheral zone 28: width 0.4 mm, radius of curvature 11.90 mm The contact lenses were worn by the patient for 7 day, at 7–8 hours a day.

After this correction period, the patient experienced a myopia and astigmatism reduction to zero power for both eyes. The far vision was 20/20 on right eye and 20/25+ on left eye. The near vision was 20/40 on right eye but was 20/20 on left eye. The patient enjoyed the simultaneous improvement of far and near visions. There are two reasons for correcting monocular presbyopia on left eye instead of on both eyes, first is for comparing the far and near vision between both eyes for demonstration, second is to preserve a clearer far vision for her occupational requirement. We learn from this case that the influence on far vision by the incorporation of tiny inner central optical zone 21a is minimal (one line decrease only). On the other hand, the quality of the near vision will be much improved (from 20/40 on right to 20/20 on left eye) by the incorporation of inner optical zone 21a. There should have been no problem fitting both eyes with dual geometric lenses if the requirement for far vision was not so critical. Otherwise we should correct the non dominant eye(left eye in this case) for reading and maintain a better far vision for the dominant sighing eye (right eye in this case).

The maintenance period (of nearly zero power) lasted for all awakening hours with a 5–7 hour maintenance night wearing. The topography of the cornea is well-centered and has a definite tiny central steeper island to support an efficient reduction in myopia and presbyopia. This case has also been followed for 3 months with no side effects.

It should be appreciated by those skilled in the art that the lenses described for Ortho-K may also be used as bi-focal contact lenses, which can be worn during daytime.

Although the present invention has been described in connection with the preferred embodiments, it will be appreciated by those skilled in the art that modifications can be made and alternatives utilized without departing from the spirit and scope of the present invention.

What is claimed is:

1. An orthokeratology contact lens for a patient's cornea, comprising:

an optical zone (20) having a curvature defined by a base curve (30), said base curve being steeper than a measured curvature (12) of a central portion of said cornea;

a plateau zone (22) coupled to said optical zone and extending radially therefrom, said plateau zone having a curvature defined by a plateau curve (34), said plateau curve being flatter than said base curve (30);

a fitting zone (24) coupled to said plateau zone and extending radially therefrom, said fitting zone having a curvature defined by a fitting curve (36), said fitting curve being steeper than said plateau curve;

an alignment zone (26) coupled to said fitting zone and extending radially therefrom, said alignment zone having a curvature defined by an alignment curve (38), said alignment curve being flatter than said fitting curve;

a peripheral zone (28) coupled to said alignment zone and extending radially therefrom, said peripheral zone having a curvature defined by a peripheral curve (42), said peripheral zone forming an edge lift to act as tear reservoir.

2. The contact lens of claim 1, wherein:

said base curve is steeper than said measured curvature by about 1–15 diopters and steeper than said plateau curve by about 3–30 diopters;

said optical zone has a width of about 3–8 mm;

said a plateau zone has a width of about 0.1–2 mm.

3. The contact lens of claim 1, wherein:

said fitting curve is about 5–30 diopters steeper than said plateau curve and about 1–25 diopters steeper than said alignment curve;

said fitting zone has a width of about 0.1–2 mm.

4. The contact lens of claim 1, wherein:

said alignment curve is about 1–30 diopters steeper than said plateau curve.

5. An orthokeratology contact lens for a patient's cornea, comprising:

an optical-plateau zone having a positive e-value to form an aspherical curve which is continuously flatter from its central to its peripheral portions, said central portion of said aspherical curve being steeper than a measured curvature (12) of a central portion of said cornea;

a fitting zone (24) coupled to said plateau zone and extending radially therefrom, said fitting zone having a curvature defined by a fitting curve (36), said fitting curve being steeper than an outmost portion of said aspherical curve;

an alignment zone (26) coupled to said fitting zone and extending radially therefrom, said alignment zone having a curvature defined by an alignment curve (38), said alignment curve being flatter than said fitting curve;

a peripheral zone (28) coupled to said alignment zone and extending radially therefrom, said peripheral zone having a curvature defined by a peripheral curve (42), said peripheral curve being flatter than said plateau curve (22) by 0–15 diopters, said peripheral zone forming an edge lift to act as tear reservoir.

6. An orthokeratology contact lens for a patient's cornea, comprising:

an optical zone, comprising an inner optical zone (20a) and an outer optical zone (21a), said inner optical zone having a curvature defined by an inner curve (30a), said outer optical zone having a curvature defined by an outer curve (31a), said inner curve being steeper than said outer curve, said outer curve being flatter than a measured curvature (12) of a central portion of said cornea, said inner zone having a width of about 0.5–1.5 mm;

a fitting zone (24) coupled to said outer optical zone and extending radially therefrom, said fitting zone having a curvature defined by a fitting curve (36), said fitting curve being steeper than said outer curve;

an alignment zone (26) coupled to said fitting zone and extending radially therefrom, said alignment zone having a curvature defined by an alignment curve (38), said alignment curve being flatter than said fitting curve;

a peripheral zone (28) coupled to said alignment zone and extending radially therefrom, said peripheral zone having a curvature defined by a peripheral curve (42), said peripheral zone forming an edge lift to act as tear reservoir.

7. The contact lens of claim 6, wherein said outer optical zone comprises a plateau zone (22) defined by a plateau curve having a same curvature as said outer curve, said plateau zone extending radially from said outer optical zone to form a continuous curve with said outer optical zone, said plateau curve being 1–4 diopters flatter than said inner curve and being 1–30 diopters flatter than said measure curvature (12) of said central portion of said cornea.

8. The contact lens of claim 7, wherein:

said plateau curve is flatter than said measured curvature by about 1–30 diopters and flatter than said inner optical zone by about 1–4 diopters;

said optical zone has a width of about 3–8 mm;

said a plateau zone has a width of about 0.1–2 mm.

9. The contact lens of claim 7, wherein:

said fitting curve is about 5–30 diopters steeper than said plateau curve;

said fitting curve is about 1–25 diopters steeper than said alignment curve;

said fitting zone has a width of about 0.1–2 mm.

10. The contact lens of claim 7, wherein:

said alignment curve is about 1–30 diopters steeper than said plateau curve.

11. The contact lens of claim 6, wherein:

said outer curve is flatter than said measured curvature by about 1–30 diopters and flatter than said inner curve by about 1–4 diopters;

said optical zone has a width of about 3–8 mm;

said a plateau zone has a width of about 0.1–2 mm.

12. The contact lens of claim 11, wherein:

said fitting curve is about 5–30 diopters steeper than said outer curve;

said fitting curve is about 1–25 diopters steeper than said alignment curve;

said fitting zone has a width of about 0.1–2 mm.

13. The contact lens of claim 12, wherein:

said alignment curve is about 1–30 diopters steeper than said outer curve.

14. A contact lens for a patient's cornea, comprising:

an inner optical zone (20b) having a curvature defined by an inner curve (30b);

an outer optical-plateau zone having a positive e-value to form an aspherical curve which is continuously flatter from a junction with said inner optical zone to its peripheral portions, said junction of said aspherical curve being one of steeper than or same as a measured curvature (12) of a central portion of said cornea;

a fitting zone (24) coupled to said plateau zone and extending radially therefrom, said fitting zone having a curvature defined by a fitting curve (36), said fitting curve being steeper than an outmost portion of said aspherical curve;

an alignment zone (26) coupled to said fitting zone and extending radially therefrom, said alignment zone having a curvature defined by an alignment curve (38), said alignment curve being flatter than said fitting curve;

a peripheral zone (28) coupled to said alignment zone and extending radially therefrom, said peripheral zone having a curvature defined by a peripheral curve (42), said peripheral zone forming an edge lift to act as tear reservoir.

15. A contact lens for a patient's cornea, comprising:

an optical zone, comprising an inner optical zone (20b) and an outer optical zone (21b), said inner optical zone having a curvature defined by an inner curve (30b), said outer optical zone having a curvature defined by an outer curve (31b), said inner curve being steeper than said outer curve, said outer curve being steeper than a measured curvature (12) of a central portion of said cornea, said inner zone having a width of about 0.5–1.5 mm, said outer zone having a width of about 1–4 mm;

a plateau zone (22) coupled to said outer optical zone and extending radially therefrom, said plateau zone having a curvature defined by a plateau curve (34), said plateau curve being flatter than said inner curve and said outer curve;

a fitting zone (24) coupled to said plateau zone and extending radially therefrom, said fitting zone having a curvature defined by a fitting curve (36), said fitting curve being steeper than said plateau curve;

an alignment zone (26) coupled to said fitting zone and extending radially therefrom, said alignment zone having a curvature defined by an alignment curve (38), said alignment curve being flatter than said fitting curve, said alignment curve being steeper than said plateau curve;

a peripheral zone (28), coupled to said alignment zone and extending radially therefrom, said peripheral zone having a curvature defined by a peripheral curve (42), forming an edge lift as tear reservoir.

16. The contact lens of claim 15, wherein said plateau zone is merged with said outer optical zone by positive e-value to form a continuously flatter aspheric curve.

17. The contact lens of claim 15, wherein:

said fitting curve is 5–30 D steeper than said plateau curve;

said fitting curve is 1–25 D steeper than said alignment curve;

said fitting zone has a width of about 0.1–2 mm.

18. The contact lens of claim 15, wherein:

said alignment curve is 1–30 D steeper than said plateau curve.

19. The contact lens of claim 15, wherein said peripheral curve is 0–15 flatter than said plateau curve.

20. The contact lens of claim 15, wherein:

said outer optical zone is steeper than said measured curvature by about 1–15 diopters, and is flatter than said inner optical zone by about 1–4 diopters;

said outer optical zone has a width of about 1–4 mm;

said outer optical zone is steeper than said plateau zone by about 3–30 diopters;

said plateau zone has a width of about 0.1–2 mm.

* * * * *